(12) United States Patent
Pacheco et al.

(10) Patent No.: US 7,763,653 B2
(45) Date of Patent: Jul. 27, 2010

(54) TERNARY AND QUATERNARY EUTECTIC MIXTURES OF LOCAL ANESTHETICS SUBSTANCES

(75) Inventors: Ogari Pacheco, Itapira (BR); Elisa Russo, Itapira (BR); Valter Russo, Itapira (BR); José Antônio Martins, Itapira (BR)

(73) Assignee: Cristalia Productos Quimicos Farmaceuticos Ltda., Itapira, SP (BR)

( * ) Notice: Subject to any disclaimer, the term of this patent is extended or adjusted under 35 U.S.C. 154(b) by 1282 days.

(21) Appl. No.: 10/557,737

(22) PCT Filed: May 21, 2004

(86) PCT No.: PCT/BR2004/000073

§ 371 (c)(1),
(2), (4) Date: Nov. 21, 2005

(87) PCT Pub. No.: WO2004/103260

PCT Pub. Date: Dec. 2, 2004

(65) Prior Publication Data

US 2006/0270736 A1        Nov. 30, 2006

(30) Foreign Application Priority Data

May 22, 2003  (BR) .................................. 0301968

(51) Int. Cl.
 A61K 31/24    (2006.01)
 A61K 9/00     (2006.01)
 A61K 9/06     (2006.01)
(52) U.S. Cl. .................. 514/537; 424/443; 424/484
(58) Field of Classification Search .................. 514/537
 See application file for complete search history.

(56) References Cited

U.S. PATENT DOCUMENTS

| 4,529,601 | A |   | 7/1985  | Broberg et al. |
| 4,562,060 | A |   | 12/1985 | Broberg et al. |
| 5,635,540 | A |   | 6/1997  | Edlich et al. |
| 5,993,836 | A | * | 11/1999 | Castillo ............ 424/401 |
| 6,031,007 | A |   | 2/2000  | Bodin et al. |
| 2002/0006435 | A1 |   | 1/2002 | Samuels et al. |

* cited by examiner

*Primary Examiner*—Jake M. Vu
(74) *Attorney, Agent, or Firm*—Birch, Stewart, Kolasch & Birch, LLP

(57) ABSTRACT

The present invention describes ternary and quaternary eutectic mixtures composed by active local anesthetic substances. These eutectic mixtures possess melting point inferior to 20° C. and consist of homogeneous liquid useful in the preparation o pharmaceutical compositions for topical anesthesia or analgesia of tissues as skin or mucous.

9 Claims, No Drawings

TERNARY AND QUATERNARY EUTECTIC MIXTURES OF LOCAL ANESTHETICS SUBSTANCES

The present invention relates to stable ternary and quaternary eutectic mixtures comprising active local anesthetic substances. These eutectic mixtures present melting point inferior to 20° C. and consist of homogeneous liquids useful to prepare pharmaceutical composition to be employed to provide topical anesthesia or analgesia of tissues such as skin and mucous.

Eutectic mixtures are combinations of two or more substances which present distinct and defined melting points and when combined in the liquid state in appropriated proportions form a homogeneous mixture with defined melting point and lower than that of its constituents.

Due to this peculiarity, the eutectic mixtures are quite promising options in the pharmaceutical field, especially considering drugs having topical application in issues such as skin and mucous which constitute true barriers to penetration of several substances.

The skin is a protector tissue that acts as a barrier to ingress of toxic and pathogenic materials and to egress (exit) of physiological fluids, and in this way, it acts also as a barrier to absorption of drugs topically administered as, for example, the anesthetics.

This tissue consists in the widest organ existing in the human body. Among the functionalized structures present therein, the vascular system, lymphatic system, glands and nerves, are detached. The nerves allow identification of various external stimuli as cold, heat, pain and pressure.

Skin is structurally composed of two tissue layers completely different from each other and bonded to each other throughout its extension. Epidermis is the most external layer, also designated stratum corneum. It is constituted of a series of epithelium stratified cell layers, whose quantity of keratin protein proportionally increases on most external layers. This special arrangement makes the most external layers more compact, offering greater protection in relation to excessive water loss, action of strange substances and organisms, besides offering greater resistance to abrasion and injuries. This layer does not contain any blood vessel and is sustained by fluids of the layer immediately below, the dermis, this one presenting irregular connection arrangements, more complex tissues and containing blood vessels in addition to a series of specialized structures.

Epidermis represents the greatest barrier to topical absorption of several drugs. This layer is composed by about 40% of lipids, 40% of proteins and 20% of water. The lipidic nature and the low water content hamper the transport of hydrophilic or charged molecules and propitiate the transport of lipophilic molecules. The absorption of hydrophilic molecules can occur through pores and sebaceous glands, but the superficial area of these structures is around 1% of total skin surface, considerably limiting the absorption of these molecules.

The topical local anesthetics development to be employed in tissues as skin depends on the anesthetic substance goes through the epidermis so that acting in the peripheral nerves, by depressing the nerves excitation or inhibiting the ionic conduction process in these peripheral nerves.

The chemical structure of most part of local anesthetics is basically composed by three groups, a lipophilic group, an intermediary chain and an ionizable group (hydrophilic group). The intermediary chain generally contains an amide or ester bond.

In the case of topical application of local anesthetics, it is observed that two factors are needed to allow the penetration through the skin: high water content and high concentration of anesthetic in its free base form. Other factor of essential importance is the physical state of the anesthetic agent which must be administered in the liquid form or dissolved in a solution.

The free base form (lipophilic) of local anesthetics, weak organic bases, is not ionized presenting a variable lipophilicity degree and dependent of the structure. This form also presents a slight or very slight solubility in water so that its use in water is unlikely. In addition to these factors, these anesthetics are solids being unlikely its employment without artifices for dissolution.

Due to high lipophilicity degree of skin, the topical local anesthetics development is primordially based on selection of lipophilic chemical structures, resulting in the administration of these substances in non ionized form (as free bases) that present preferential penetration through that tissue.

The preparation of local anesthetics for topical anesthesia of tissues as skin is a field where eutectic mixtures present an important potential. The obtainment of eutectic mixtures with low melting point, preferably lower than room temperature, makes possible to prepare pharmaceutical composition in the form of oil in water emulsions, enabling a maximized activity of these compositions by employing the lipophilic form of the anesthetic and water which is need to help the permeation of the active substance through skin.

Among the products currently employed in topical anesthesia available in the market there is the product known as EMLA®, which is a cream wherein the anesthetics substances lidocaine and prilocaine are employed in the composition as a eutectic mixture of two components with low melting point.

The use of eutectic mixtures is of particular interest in liquid compositions, especially when these mixtures have low melting point so that they present liquid physical aspect at room temperature.

There are some references that describe the preparation of binary eutectic mixtures of local anesthetic substances, which are employed in topical anesthesia of skin and mucous. However, up to now, there isn't description of more complex eutectic mixtures constituted of three or more local anesthetic substances, which are designated as ternary or quaternary eutectic mixtures.

Due to different characteristics inherent to each local anesthetic, there is interest in prepare more complex combinations of these substances so that provide a modulation of anesthetic and/or analgesic effect.

Each local anesthetic currently available presents a particularity which makes it more appropriated to specific procedures. Such differences relates to the onset time of anesthetic effect, time of duration and intensity of anesthesia.

Among the references in literature describing eutectic mixtures employed in topical anesthesia, there are the U.S. Pat. Nos. 4,562,060 and 4,529,601 (both of Broberg et al), which describe eutectic mixtures of local anesthetics having low melting point. The eutectics proposed in this invention are binary eutectics, that is, constituted of combinations of two local anesthetic substances. The eutectic mixtures described present melting point ranging from 17° C. to 34° C. and are constituted basically of the combination of prilocaine with others anesthetics substances in a ratio from 42:58 to 80:20 respectively, particularly emphasizing the eutectic mixture of prilocaine and lidocaine which is the base of the marketed composition known as EMLA®. These patents don't mention about the preparation of more complex eutectic mixtures.

The U.S. Pat. No. 5,993,836 (Castilho) describes the preparation of a binary eutectic of lidocaine and prilocaine in a ratio of 3:1 respectively. As in the earlier case, there is no mention about more complex eutectics.

The U.S. Pat. No. 5,635,540 (Edlich et al.) describes a binary eutectic constituted of lidocaine and prilocaine or prilocaine and tetracaine also employed in the lipophilic form (free base) as in the earlier references. In this document there is no mention about preparation of more complex eutectics.

The U.S. Pat. No. 6,031,007 (Brodin et al.) describes the use of an eutectic of prilocaine and lidocaine in the ratio of 1:1 respectively. In order to differentiate its matter of invention from the U.S. Pat. Nos. 4,562,060 and 4,529,601, the authors use surfactant agents to obtain a better composition performance and agents that confer to composition a thermo reversible gelling properties. Also in this document there is no mention about preparation of more complex eutectics.

The U.S. application 20020006435 describes the use of a binary eutectic of lidocaine and prilocaine in the ratio ranging from 1:4 to 4:1 respectively. In this patent, the author cites the possibility of associate the anesthetics in an eutectic mixture constituted of prilocaine, lidocaine and dibucaine. However, there is no mention about the quantity of each substance to form such ternary eutectic mixture and neither the temperature in which such eutectic is present in liquid form.

In despite of eutectic mixtures constitute a promising field to topical use of several drugs, they have been few explored with that purpose in the pharmaceutical development.

The objective of the present invention is the preparation of ternary and quaternary eutectic mixtures, constituted of local anesthetic substances. These eutectic mixtures are characterized by having melting point below of 20° C., being liquids at room temperature, and stable when stored at room temperature or under refrigeration.

The advantages of associate three or more local anesthetic substances to improve topical anesthesia originate from the possibility of use the differences of activity inherent to each local anesthetic.

According to literature, the anesthetic substances are distinguished by means of the chemical structure of the anesthetic and the therapeutic effect provided. Thus, there are anesthetic substances that present a fast installation (low latency), intense and short effect, establishing a fast anesthesia of short duration. There are also substances that present an intermediary time of action and a superior latency. There are yet anesthetic substances that present a long time of anesthetic activity and latency.

The combination of different anesthetic substances offer the possibility of obtain a modulated effect during the total period of anesthesia by combining anesthetics that present low latency and short duration, anesthetics of intermediary duration and anesthetics of long duration, so that modulating and prolonging the anesthesia.

According to the present invention it is possible prepare ternary and quaternary eutectic mixtures when their constituents are combined in appropriated proportions. In the present invention, the components of the mixture are all solids at room temperature previous to formation of the mixture, but after the melting and dissolution of the components, on returning to room temperature, they keep in liquid state without occurrence of any component crystallization.

The formation of the eutectic mixture depend of the proper concentration of its constituents, which must promote the formation of intermolecular forces probably originated of interactions known as hydrogen bridges or Van Der Waals forces, these ones which neutralize or countervail to usual forces of each component in the formation of crystalline forms. The formation of these forces are provided by combining the substances, at molecular level, through melt of the constituents or use of organic solvents, the last one comprising the dissolution of the substances followed by elimination of said solvent and consequent eutectic formation.

According to the present invention, the eutectic mixtures of local anesthetics are constituted by anesthetics of ester and/or amide type, which are employed in its lipophilic forms, that is, in its free base forms.

Among the proper substances to preparation of eutectic mixtures of the present invention, the substances known by its generic names as prilocaine, lidocaine, bupivacaine, tetracainem benzocaine, ametocaine, mepivacaine, dibucaine, etidocaine, butanilicaine and trimecaine are detached.

Preferably the eutectic mixtures of the present invention are prepared by combining prilocaine, lidocaine, bupivacaine and/or tetracaine, whose generic and chemical names, CAS number and melting point are presented in table 1 below:

TABLE 1

Local Anesthetics - generic and chemical names, CAS number and melting point.

| Generic Name | Chemical Name | CAS Number | Melting Point |
| --- | --- | --- | --- |
| Lidocaine | 2-(diethylamino)-N-(2,6-dimethylphenyl)-acetamide | 137-58-6 | 68-69° C.[1] |
| Prilocaine | N-(2-methylphenyl)-2-2(propylamino)propanamide | 721-50-6 | 37-38° C.[1] |
| Bupivacaine | 1-Butyl-N-(2,6-dimethylphenyl)-2-piperidinocarboxamide | 2180-92-9 | 107.5-108° C.[1] |
| Tetracaine | 4-(butylamino)benzoic acid 2-(dimethyl-amino)ethyl ester | 94-24-6 | 41-46° C.[2] |

[1]Merck Index Version 12:3.
[2]USP Pharmacopoeia XXIII, page 1503.

By combining the substances presented on table 1 in appropriated proportions, it is possible obtain ternary and quaternary stable eutectic mixtures having melting point below the room temperature, which are presented as a lipophilic liquid appropriated to preparation of liquid pharmaceutical composition.

According to the present invention, the ternary eutectic mixture present as constituents the active ingredients known by the generic names of prilocaine, lidocaine, bupivacaine or tetracaine, three to three combined. Preferably the ternary eutectic mixture is constituted by combining these substances in the following proportions:

(a) Prilocaine/lidocaine/bupivacaine in a weight ratio of 20-80%/15-55%/5-25%, respectively;

(b) Prilocaine/tetracaine/bupivacaine in a weight ratio of 30-70%/10-50%/5-35%, respectively;

(c) Prilocaine/tetracaine/lidocaine in a weight ratio 20-70%/10-50%/10-40%, respectively.

The proportion between the local anesthetic substances present in the ternary eutectic mixture is most preferably:

(d) Prilocaine/lidocaine/bupivacaine in a weight ratio of 40-60%/25-45%/10-25%, respectively;

(e) Prilocaine/tetracaine/bupivacaine in a weight ratio of 40-60%/20-40%/10-35%, respectively;

(f) Prilocaine/tetracaine/lidocaine in a weight ratio of 40-60%/20-40%/20-30%, respectively.

According to the present invention the quaternary eutectic mixture of local anesthetic is obtained by combining preferably the anesthetics prilocaine, lidocaine, bupivacaine and tetracaine.

The proportion of anesthetic substances that compose the quaternary eutectic mixture is preferably:

(g) Prilocaine/lidocaine/bupivacaine/tetracaine in a weight ratio of 10-40%/5-35%/2-18%/30-70%, respectively.

The proportion of anesthetic substances that compose the quaternary eutectic mixture is most preferably:

(h) Prilocaine/lidocaine/bupivacaine/tetracaine in a weight ratio of 15-35%/10-25%/5-15%/40-60%, respectively.

The eutectic mixtures described in the present invention are prepared through combination of the anesthetic agents in its free base form and in solid state. This mixture is heated until it reaches the melting of the agent having the lower melting point. Said agent, once melted, provide a medium in which the others substances are soluble, being possible the dissolution of the others anesthetics agents with formation of a homogeneous oil. Optionally, the agent having the lower melting point is melted alone and the other agents are sequentially added to the resulting oil to promote the formation of the homogenous solution. In this case the addition order of the other agents is not specific, but it is convenient to follow the sequence established by the melting point of each substance, adding in the sequence the agents of lower melting point to the agent of higher melting point.

Alternatively, the eutectic mixtures of the present invention are prepared by employing an appropriated organic solvent in which the anesthetic substances are dissolved producing a diluted solution of them. The organic solvent is completely removed by distilling under reduced pressure and low temperature, resulting in the eutectic mixture in homogeneous oil form. Among the appropriated organic solvents used to prepare the eutectic mixtures of the present invention, ethyl ether, methyl t-butyl ether, ethanol, propanol, isopropanol, acetone, dichloromethane and chloroform are detached. All theses solvents present considerably low melting point and are easily eliminated by distilling under reduced pressure (under vacuum) and temperature.

The temperature employed to promote the heat and preparation of the eutectic mixtures described is about 40° C. Any equipment or method of heat is adequate to prepare these eutectic mixtures, being preferably employed equipment and methods which can promote the control and monitoring of the heat temperature. For example, to prepare the eutectic mixtures described in the experimental part, a thermostatized water-bath to control the temperature and a mechanical agitator to homogenize the mixture were employed.

The local anesthetics in its free base forms (not ionized), in general, are substances which present slight or very slight solubility in water or solvents considered proper and safety to topical administration. Due to this factor, pharmaceutical compositions elaborated with these substances are difficult to formulate, since the non-ionized form don't have total solubility in the composition, it exist indeed as solid micro particles which in this physical state are not able to properly penetrate through skin.

The ideal form to prepare compositions for topical administration is employing substances which are in liquid form, preferably at temperatures near to that of skin, favoring considerably its penetration through that tissue. However, the local anesthetics in their non-ionized form (free bases) are solids with melting point much high when compared to the normal corporeal temperature. Due to this factor several anesthetics compositions for topical administration were developed by micro dispersing the anesthetic in a series of excipients. However, the efficacy of such compositions is usually considered unsatisfactory as a consequence of low transport through epidermis of anesthetic substances at solid state.

The use of the eutectic mixtures described in the present invention provide a consistent advance for obtaining more proper pharmaceutical compositions to topical anesthesia, eliminating the inconveniency of work with the anesthetics substances in their ionized form (hydrophilic, saline) or crystalline micro dispersion of their free base forms (lipophilic, non-ioneized), since both are inadequate to topical anesthesia. As these eutectic mixtures are liquids at room temperature and are prepared employing the anesthetics substances in free base forms, they are more adequate to be used in topical anesthesia because of their higher penetration through tissues like skin and mucous.

The ternary and quaternary eutectic mixtures of local anesthetic substances described in the present invention are useful in anesthesia and analgesia of tissues as skin and mucous. The anesthesia and analgesia provided by these local anesthetic mixtures include both uninjured and injured tissues, the last ones being those having suffered lacerations, punctures, burns, incision or others injuries that had disrupted the tissue integrity.

The eutectic mixtures of the present invention can be employed in several areas of medicine such as dermatology, urology, gynecology, gastroenterology, odontology, otorhinolaryngology, coloproctology, proctology among several others.

The administration of eutectic mixtures of the present invention can be effected in their pure form, that is, without addition of excipients. Other embodiment of administration of the eutectic mixtures of the present invention consist in the preparation of emulsions or solutions in which they are diluted and/or aggregate to excipients that can provide the necessary dilution and the more proper physical characteristic to the kind of procedure or local administration. In these cases, the eutectic mixtures of local anesthetics can be formulated in the form of solutions proper to aspersion to tissues, lotions, gels and creams of variable consistency for localized administration (in case of a more prolonged permanency in contact with the tissue is desired), gather to device of transdermal application (transdermal patches), in the form of varied emulsions, etc.

When gathered to pharmaceutical excipients to provide the necessary dilution to administration of therapeutic dose to the tissue, the ternary or quaternary eutectic mixtures can be employed in concentrations ranging from 0.01% to 80% in relation to total weight of composition. Preferably, the concentration ranges from 0.01% to 40% in weight of composition. More preferably the concentration of the ternary or quaternary eutectic mixtures ranges from 0.1 to 20% in weight of final pharmaceutical composition.

The eutectic mixtures of the present invention can be employed for preparation of pharmaceutical composition based on water or compositions wherein the solvent is an organic solvent selected from the pharmaceutical acceptable organic solvents and mixtures between water and these solvents.

Several excipients can be employed with the pharmaceutical compositions prepared with the eutectic mixtures of the present invention, being these excipients selected from those having physical-chemical compatibility with the eutectic mixture ingredients. These excipients are selected in function of the required form of the final pharmaceutical composition which include but is not limited to solutions, lotions, creams, gels, paste, ointment, spray and others.

The excipients included can be emollients, emulsifiers, humectants, surfactants/surface active, thickener, flavoring, coloring, substances for adjust the pH as alkalizing and acidifiers, buffers, other solvents as lower alcohols, glycols and polyols, in addition to oils and grease.

The emollient agents tend to lubricate and protect the skin. Among them, the pharmaceutical compositions prepared with the eutectic mixtures of the present invention can comprise silicone oils such as dimethicone, cyclomethicone and dimethiconol, highly ramified hydrocarbons, wax Uniox C and/or combinations among them.

The humectants are employed in order to avoid exsiccating or dehydration of skin. Among them, the pharmaceutical compositions prepared with the eutectic mixtures of the present invention can comprise polyhydroxyalcohols such as sorbitol, glycerin polypropylene glycols, hexanetriol and propylene glycol.

Surfactants agents, also known as surface active agents, are substances having the property of reduce the surface tension of pharmaceutical composition when in contact with the skin, favoring the absorption. The pharmaceutical compositions prepared with the eutectic mixtures of the present invention can comprise the anionic, cationic and non ionic surfactants such as polyoxyethylene derivatives of alkylethers (for example Steareth, Ceteth), polyoxyethylene derivatives of castor oil (for example Cremophor family), polyoxyethylene stearate (for example Myrj, Crodet), polyoxyethylene derivatives of sorbitol fatty esters and anhydrides thereof (for example Tween, Spam, Octoxynol), fatty derivatives of glycerides (for example Arlacel), copolymers of polyoxyethylene-polyoxypropylene (for example Poloxamer) and/or mixtures between these substances.

Thickener agents are employed to give proper consistency to administration in several regions. The pharmaceutical compositions prepared with the eutectic mixtures of the present invention can comprise as thickener methylcellulose, hydroxyethylcellulose, hydroxypropylmethylcellulose, carboxy-methylcellulose, xanthan gum, carbomer and/or mixtures between these agents.

The pharmaceutical compositions prepared with the eutectic mixtures of the present invention can also comprise preserving or stabilizing agents pharmaceutically acceptable, in order to increase its physical-chemical and microbiological stability. The stabilizers employed can be parabens, benzyl alcohol, chorobutanol, chlorocresol, cresol, benzethonium chloride, benzalkonium chloride and or combinations between these agents.

The pharmaceutical compositions prepared with the eutectic mixtures of the present invention can comprise flavoring and sweet-smelling agents which give pleasant flavor and aroma to varied administrations (for example in case of use in the buccal cavity).

Alkalizing or acidifiers agents and buffers can be employed to adjust the composition pH which is dependent of the region in which the product will be administered.

In addition to these excipients, pharmaceutical acceptable coloring agents can be employed in the pharmaceutical compositions of the present invention, being its use especially indicated to highlight a region of administration of these compositions.

The present invention is in the following more particularly described in form of illustrative examples, but not exhaustive examples, of ternary and quaternary eutectic mixtures of local topical anesthetics of the present invention. All percentages are given in weight.

Preparation of the Ternary and Quaternary eutectic Mixtures of the Examples 1-16

The anesthetics substances listed in the examples 1-10 were prepared according to one of the following general methods:

General Method I:

The free bases of anesthetics substances were weighted in the proportions indicated in percentage in weight in a glass container which was brought to a thermostatized water bath. The homogenization of substances was effected by means of mechanical stirring while the medium was heated at a temperature around 40° C. The resulting limpid and homogeneous liquid was divided and stored in two glass container with cover. The container 1 was kept in observation and stability at room temperature (temperature between 20 and 30° C.) and the container 2 was kept in observation and stability under refrigeration (temperature between 4 and 8° C.).

General Method II:

The free bases of anesthetics substances of lower melting point were weighted in the percentage in weight indicated in the respective example and placed in a glass container which was taken to a thermostatized water bath. The container was heated at an approximated temperature around 40° C. and kept under stirring. After melting, the others substances were sequentially added in an increasing order of melting point, while the medium was kept at temperature around 40° C. and under stirring. The heating and stirring was kept until formation of a limpid and homogeneous liquid. These liquid was fractioned in two glass containers. The container 1 was kept in observation and stability at room temperature (temperature between 20 and 30° C.) and the container 2 was kept in observation and stability under refrigeration (temperature between 4 and 8° C.).

Table 2 below list the anesthetics substances and the percentage in weight respectively employed to the preparation of the ternary eutectic mixtures of examples 1 to 10:

TABLE 2

Examples 1 to 10

| Examples | Anesthetics | Composition (% in wheight) | T room | T refrig. |
|---|---|---|---|---|
| 1 | Bupivacaine:prilocaine:lidocaine | 15:40:45 | $S_H$ | $S_P$ |
| 2 | Bupivacaine:prilocaine:lidocaine | 15:50:35 | $S_H$ | $S_P$ |
| 3 | Bupivacaine:prilocaine:lidocaine | 15:60:25 | $S_H$ | $S_P$ |
| 4 | Prilocaine:lidocaine:bupivacaine | 50:30:20 | $S_H$ | $S_P$ |
| 5 | Bupivacaine:prilocaine:tetracaine | 15:40:45 | $S_H$ | $S_P$ |
| 6 | Bupivacaine:prilocaine:tetracaine | 15:50:35 | $S_H$ | $S_P$ |
| 7 | Bupivacaine:prilocaine:tetracaine | 15:60:25 | $S_H$ | $S_P$ |
| 8 | Prilocaine:tetracaine:lidocaine | 60:20:20 | $S_H$ | $S_P$ |
| 9 | Prilocaine:tetracaine:lidocaine | 46:27:27 | $S_H$ | $S_P$ |
| 10 | Prilocaine:tetracaine:lidocaine | 40:40:20 | $S_H$ | $S_P$ |

$S_H$: soluble, homogeneous phase;
$S_P$: precipitate when stored in refrigerator (temperature between 4° C. and 8° C.).

All of the eutectic mixtures prepared in the examples from 1 to 10 that were kept at room temperature presented physical-chemistry stability after 180 days of observation, without any visible crystalline formation.

EXAMPLE 11-16

Quaternary Eutectic Mixture

The quaternary eutectic mixtures were prepared according to general methods I or II described above.

Table 3 below lists the proportions of active substances employed in the preparation of the eutectic mixtures of the examples 11 to 16.

TABLE 3

Examples 11 to 16

| Examples | Anesthetics | Composition % in wheight | T room | T refrig. |
|---|---|---|---|---|
| 1 | Prilocaine:lidocaine:bupivacaine:tetracaine | 25:20:5:50 | $S_H$ | $S_P$ |
| 2 | Prilocaine:lidocaine:bupivacaine:tetracaine | 25:17.5:7.5:50 | $S_H$ | $S_P$ |
| 3 | Prilocaine:lidocaine:bupivacaine:tetracaine | 25:18:10:47 | $S_H$ | $S_P$ |
| 4 | Prilocaine:lidocaine:bupivacaine:tetracaine | 20:15:10:55 | $S_H$ | $S_P$ |
| 5 | Prilocaine:lidocaine:bupivacaine:tetracaine | 30:15:10:45 | $S_H$ | $S_P$ |
| 6 | Prilocaine:lidocaine:bupivacaine:tetracaine | 25:15:15:45 | $S_H$ | $S_P$ |

SH: soluble, homogeneous phase

The quaternary eutectic mixtures of examples 11 to 16 demonstrated stability when stored in refrigerator or at room temperature during 180 days, without any evidence of crystallization or degradation.

The invention claimed is:

1. A ternary eutectic mixture comprising the free bases of the local anesthetics prilocaine, lidocaine and bupivacaine in a weight ratio of 40-60%/25-45%/10-25%, respectively, the resulting mixture being a homogenous liquid having a melting point below 20° C.

2. The ternary eutectic mixture according to claim 1, that is prepared by mixing the local anesthetic substances in their free base forms in a solid state, and transforming them into a homogeneous liquid by heating at a temperature of around 40° C.

3. The ternary eutectic mixture according to claim 1, that is prepared by mixing the local anesthetics in their free base forms dissolved in one or more organic solvents and removing said one or more organic solvents at a temperature below 40° C. under vacuum.

4. A pharmaceutical composition comprising the ternary eutectic mixture of claim 1 and at least one pharmaceutical excipient.

5. The pharmaceutical composition according to claim 4, in which the ternary eutectic mixture is present in an amount from 0.01 to 99% by weight of the final pharmaceutical composition.

6. The pharmaceutical composition according to claim 4, in which the ternary eutectic mixture is present in an amount from 0.01 to 80% by weight of the final pharmaceutical composition.

7. The pharmaceutical composition according to claim 4, in which the ternary eutectic mixture is present in an amount from 0.01 to 40% by weight of the final pharmaceutical composition.

8. The pharmaceutical composition according to claim 4, in which the ternary eutectic mixture is present in an amount from 0.1 to 20% by weight of the final pharmaceutical composition.

9. A method of obtaining local anesthesia in mammals comprising topically administering to a patient a ternary eutectic mixture of the free bases of the local anesthetics prilocaine, lidocaine and bupivacaine employed in a weight ratio of 40-60%/25-45%/10-25%, respectively, the resulting mixture being a homogenous liquid having a melting point below 20° C.

* * * * *